US008865397B2

(12) United States Patent
Mueller et al.

(10) Patent No.: US 8,865,397 B2
(45) Date of Patent: Oct. 21, 2014

(54) METHOD FOR COOLING AN ORGAN WITH A TRANSPARENT COOLING GEL

(71) Applicant: Fresenius Kabi Deutschland GmbH, Bad Homburg (DE)

(72) Inventors: Bernd W. Mueller, Peine (DE); Klaus Sommermeyer, Rosbach v.d.H (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 14/098,903

(22) Filed: Dec. 6, 2013

(65) Prior Publication Data

US 2014/0093863 A1 Apr. 3, 2014

Related U.S. Application Data

(62) Division of application No. 12/733,970, filed as application No. PCT/EP2008/007789 on Sep. 17, 2008, now abandoned.

(30) Foreign Application Priority Data

Oct. 1, 2007 (DE) .................. 10 2007 047 040

(51) Int. Cl.
*A01N 1/02* (2006.01)
(52) U.S. Cl.
CPC . *A01N 1/021* (2013.01); *A01N 1/02* (2013.01)
USPC .......................................................... 435/1.1
(58) Field of Classification Search
CPC ................................................... A01N 1/021
See application file for complete search history.

(56) References Cited

U.S. PATENT DOCUMENTS

| | | | |
|---|---|---|---|
| 2,827,419 A | 3/1958 | Tourtellotte et al. | |
| 4,061,537 A * | 12/1977 | Seiler et al. | 435/1.1 |
| 4,604,379 A | 8/1986 | Twardowski et al. | |
| 6,352,707 B1 * | 3/2002 | Usala | 424/423 |
| 2001/0049140 A1 | 12/2001 | Baust et al. | |
| 2004/0053205 A1 | 3/2004 | Potts et al. | |
| 2004/0053207 A1 * | 3/2004 | Griffiths et al. | 435/2 |
| 2005/0119170 A1 | 6/2005 | Bouwstra et al. | |
| 2005/0288235 A1 | 12/2005 | Zhao | |

FOREIGN PATENT DOCUMENTS

| | | |
|---|---|---|
| DE | 3500268 | 7/1986 |
| DE | 19907257 | 9/2000 |
| EP | 0187361 | 7/1986 |
| EP | 1250041 | 10/2002 |
| GB | 1313164 | 4/1973 |
| GB | 1556199 | 11/1979 |
| HU | 52805 | 8/1990 |
| JP | 8009966 | 1/1996 |
| WO | 00/25580 | 5/2000 |
| WO | 00/48637 | 8/2000 |
| WO | 00/53008 | 9/2000 |

OTHER PUBLICATIONS

Hosgood et al., Effects of arterial pressure in an experimental isolated haemoperfused porcine kidney preservation system, 2006, British Journal of Surgery 93(7): 879-884.*
Haemaccel Product Information Sheet, AFT Pharmaceuticals Ltd. 2005.
Product Literature for Gelifundol®, Biotest Pharmaceuticals, 1993.
Product Literature for Hextend®, BioTime, Inc., 1999.
Product Literature for Gelofusine®, B. Braun, 2002.
Pegg et al., "Hypothermic Perfusion of Rabbit Kidneys with Solutions Containing Gelatin Polypeptides," Division of Cryobiology, vol. 24, No. 1, pp. 29-38, 1977.
Serrou et al., "Eight-and Twenty-Four-Hour Canine Pancreas Preservations Using a Simple Gel Cooling Technique," Department of Immunology, vol. 16, No. 5, pp. 398-402, 1973.
Vars et al., "Various Plasma Expanders in Animals," 1952, Annals of the New York Academy of Sciences, 55: 496-503.

* cited by examiner

*Primary Examiner* — Jon P Weber
*Assistant Examiner* — Robert Yamasaki
(74) *Attorney, Agent, or Firm* — Occhiuti & Rohlicek LLP

(57) ABSTRACT

For cooling organs and tissues in transplantation medicine, only ice preparations are used so far which are not soft like a gel and are brought to the necessary degree of comminution by mechanically comminuting frozen, sterile, pyrogen-free isotonic infusion solutions, such as 5% glucose or 0.9% saline, with great effort. The lack of gel-like consistency of the preparations and the expensive production process are very disadvantageous.
Therefore, it was necessary to produce a cooling preparation for transplantation medicine, which in a temperature range from −5° C. to 4° C. is gel-like and soft, transparent and sufficiently mechanically stable and yet remains formable. In accordance with the invention, such preparation can be produced from gelatin solutions in the concentration range of 3-20 wt-%, which are isotonized or adjusted to 280-650 mosmol/kg and are almost pH-neutral, by simple cooling and/or freezing.

13 Claims, No Drawings

METHOD FOR COOLING AN ORGAN WITH A TRANSPARENT COOLING GEL

CROSS REFERENCE TO RELATED APPLICATIONS

This application is a divisional of U.S. application Ser. No. 12/733,970, filed on Jul. 30, 2010 which is a National Stage of International Application No. PCT/EP2008/007789 filed on Sep. 17, 2008, which claims priority to German Application No. 10 2007 047 040.3 filed Oct. 1, 2007, the contents of which are hereby incorporated by reference in their entirety.

This invention relates to the technical field of cooling organs in transplantation medicine, in particular to a cooling gel.

In transplantation medicine, cooling the tissue or organ to be transplanted is a common measure to reduce the speed of metabolic processes and achieve a preservation of the organs. Temperatures as low as −5° C. are achieved by means of finely crushed ice preparations. Since it is necessary to work in a sterile environment, this finely crushed ice usually is produced by freezing sterile isotonic saline or 5% glucose solution, which are commercially available as infusion solutions filled in bags.

Freezing is effected in the packaging material at temperatures ←15° C. in a deep freezer. Subsequently, the ice block obtained is converted into a finely crushed ice slush by applying mechanical energy onto the bag, such as a hammer blow. Subsequently, the comminuted ice is removed in a sterile environment and the organ or tissue is treated with the same.

The crushed ice is subject to further requirements. First of all, it should be comminuted so fine that it can be formed around the organ region and can also be placed around smaller areas. Furthermore, the aqueous solution obtained when melting the ice slush should rather have a pH in the range between 5 and 7 and should be approximately isotonic, i.e. should rather have physiological conditions, so as not to damage the tissue. All substances obtained must be medically compatible, so that the rest of the thawed solution possibly left in the operating area does not present a risk. The latter is achieved by freezing isotonic, pH-neutral 0.9% saline or e.g. also a 5% glucose solution, which are employed as infusion solutions. After melting such solutions, the same are physiologically well-tolerated and do not damage the organs.

However, the ice mixtures described above have the disadvantage that they are not optimal in mechanical terms for enclosing e.g. small organ areas, i.e. they have no flexibility.

EP 1 649 842 describes the use of a cooling gel for cooling organs as a cooling material in an envelope suitable for this purpose. The direct contact of the cooling gel with the organ is not described. Moreover, there is not disclosed a composition which is particularly suitable for such purpose.

EP 970 707 describes a gelatin-based cooling gel. The cooling gel described there neither is used for cooling organs nor is the composition adapted for such application.

Therefore, it has been the object to find a greatly formable and transparent cooling preparation which is suitable for cooling organs in transplantation medicine, when a direct contact is made between the organ and the cooling preparation. The object also comprises the production of such cooling preparation.

Furthermore, it has been the object to find an advantageous method for cooling organs before and during the transplantation, which avoids the disadvantages of cooling with crushed ice, namely low formability and low transparency.

The objects advantageously are solved by the cooling gel of claim 1 and its production according to claim 7 as well as the method for cooling an organ according to claim 10.

A cooling gel of the invention is soft and formable at temperatures between −5° C. and +4° C. and while being physiologically acceptable, also has the necessary cold capacity for cooling organ and tissue regions. Advantageously, such cooling gel is liquefied at temperatures >5° C. and easily runs off from the organs after thawing and thus is easily removable. Expediently, the preparation exclusively contains non-toxic constituents, so that, in case residual amounts are left in the organism after performing the cooling, the same is completely harmless.

Such cooling gel has a gelatin content of 3-20 wt-%, preferably between 6 and 10 wt-%. Such composition advantageously contains electrolytes which are physiologically acceptable, such as sodium, potassium, magnesium, calcium and lactate, at least are isotonized, but possibly can also be enriched up to an osmolarity of 600 mosmol/kg. The gelling range of such gels ideally lies between +5° C. and −5° C. Succinyl gelatin is a gelatin cross-linked by succinic acid. In particular cooling gels in which succinyl gelatin is used as gelatin therefore have an ideal mix of mechanical stability and good formability within the highly relevant temperature range of −5° C. to +4° C. and in addition have a good cooling capacity.

A cooling preparation of the invention can be produced from an aqueous solution, be filled in plastic containers and sterilized, similar to the case of known gelatin preparations which are used as plasma volume substitute. In a preferred embodiment, the cooling preparation only consists of gelatin or gelatin derivatives, lactate and electrolytes. Electrolytes preferably are contained in the following concentrations: 150-300 mmol/l sodium, 5-10 mmol/l potassium, 1.5-3 mmol/l magnesium, 1.5-3 mmol/l calcium, 100-200 mmol/l chloride. Lactate preferably is contained in the concentration of 30-60 mmol/l.

The compositions of the invention differ from the latter preparations by the much higher content of gelatin derivative and possibly also by the higher content of electrolytes.

The aqueous solution thus obtained is filled in a container, such as a polyethylene or PVC bag, and is converted into the transparent gel form at temperatures of −8° C. to 3° C. (e.g. by putting it into a freezer adjusted to the corresponding temperature). Preferably, gelling is performed at temperatures of −5° C. to 1° C.

Alternatively, the preparation can be deep-frozen at −10° C. to −30° C., preferably −15° C. to −20° C., particularly preferably at approximately −18° C., and the deep-frozen hard preparation can then be heated to a temperature of −5° C. or more and thus be transferred into a gel-like consistency. At room temperature, a mechanically easily formable structure thus is assumed within about 60 minutes, which is transparent. This mass can be stored in a refrigerator at temperatures of −5° C. to 4° C. for up to 24 hours, and in this period it can be used as a cooling preparation.

A deep-frozen preparation can also be put into a refrigerator of 2-8° C. Within about 12 hours, the same assumes a formable, transparent gel-ice structure which can likewise be used as a cooling preparation within the following 24 hours.

Gelatin is a collagenic protein. In contrast to gelatin, collagen occurring in the animal body is not water-soluble. It consists of triple helices of the collagenic proteins, which congregate to collagen fibrils and thus form bones, cartilages, vessels etc. Gelatin usually is obtained from animal collagen, frequently from pork rinds, but every gelatin from natural collagen is suitable for the invention. In the production of gelatin, collagen first is digested and the triple helices are broken up. The collagenic protein thus is transferred into a water-soluble form. With correspondingly high gelatin concentrations in the solution, the collagenic proteins are cross-linked at lower temperatures and form a gel-like consistency. The properties of the natural gelatin can be changed by adding an agent to the gelatin which changes the cross-linking properties of the gelatin. By using such cross-linking agents, such as urea or succinic acid (succinyl acid) or its salt, gelatin derivatives are obtained.

The use of gelatin or gelatin derivatives in medical solutions is known from commonly used plasma or blood volume expanders. These solutions can contain gelatin derivatives such as succinyl gelatin, oxypolygelatin or urea cross-linked gelatin solutions, but differ from the preparations of the invention by the much smaller concentration range of the gelatin derivative.

The invention is practicable for the skilled person by varying said parameters for each physiologically acceptable cross-linked gelatin. Surprisingly, however, it has been found that succinyl gelatin, compared to natural gelatin, urea cross-linked gelatin or oxypolygelatin, is particularly useful to form mechanically sufficient gels at deep temperatures. Such cooling preparations on the basis of succinyl gelatin, as compared to cooling preparations with other gelatins or derivatives thereof, have a particularly wide relevant temperature range in which the gel-like condition undergoes an ideal compromise between formability and mechanical stability for the purpose of cooling organs.

In the relevant temperature range of −5° C. to +5° C., cooling gels on the basis of succinyl gelatin also have an excellent cooling capacity. The term succinyl gelatin describes a gelatin derivative cross-linked with succinic acid or its salt or succinic anhydride, and the term gelatin succinate also is used as a synonym.

The preparations of the invention ideally should be sufficiently liquid at room temperature, so that they can easily be removed again from the cooled organ area. In addition, the liquid phase offers the advantage at room temperature that such solutions can be filled or produced more easily.

Upon freezing, gelatin concentrations below 3%, like those of commercially available gelatin infusion solutions used as plasma volume expanders, do not lead to gels with the desired mechanical stability and, depending on their chemical structure, in part form gels only with difficulty. Such preparations pass over too fast, i.e. within an only small temperature range, from a highly formable but mechanically not sufficiently stable condition into a mechanically highly stable non-formable condition.

The addition of an electrolyte to obtain blood-isotonic conditions at the same time decreases the crystallization temperature of the ice, which beside the production of physiological conditions is a desirable effect, since the onset of the crystallization of ice makes the gel intransparent and hard.

By adding an electrolyte, the osmolality can be adjusted up to 650 mosmol/kg, since such a range still is acceptable for infusions which are injected into a peripheral vein. An osmolality in the range from 280-600 is preferred, and a range from 400-550 mosmol/kg is particularly preferred. At the same time, the crystallization temperature of the ice can be adjusted correspondingly.

Gelatin preparations with gelatin succinate with a concentration >3% are quite particularly preferred. This gelatin derivative forms mechanically sufficiently stable gels already at relatively low concentrations as compared to oxypolygelatin derivatives and urea cross-linked gelatin preparations.

The strength of the gelatin preparations can be increased up to a content of 3 mmol/l by a physiological addition of magnesium or calcium. The preferred solutions can be prepared from photogelatin, although all natural gelatins and their derivatives can be used. Gelatins or gelatin derivatives with a mean molecular weight of 25-45 kD are preferred. The same are dissolved in water for injections and possibly decomposed thermally, thereafter cross-linked or derivatized with succinic anhydride.

The solutions can be depyrogenized by means of hydrogen peroxide.

After addition of the electrolytes for obtaining isotonic conditions or of calcium or magnesium, the solution ideally is sterile-filtered, filled in plastic containers and/or heat-sterilized.

EXAMPLE 1

500 ml of a 3% solution of gelatin succinate with 150 mmol/l sodium, 5 mmol/l potassium, 1.5 mmol/l magnesium, 100 mmol/l chloride and 30 mmol/l lactate are put into a freezer adjusted to −18° C. After 2.5 hours, the solution containing succinyl gelatin is converted into a transparent gel. The gel obtained from the succinyl gelatin is highly formable and has a low mechanical stability; the resulting gel still has a slight tendency towards flowing. With extended storage in a freezer, the mechanical stability is slowly increasing.

EXAMPLE 2

Both a 6% and a 9% aqueous solution of succinyl gelatin with the electrolyte concentrations of 300 mmol/l sodium, 10 mmol/l potassium, 3 mmol/l magnesium, 200 mmol/l chloride and 60 mmol/l lactate each is put into a freezer with −18° C. and gel formation is observed over time.

The 9% solution becomes gel-like after about 1 hour, whereas the 6% solution only forms a gel after 2 hours. After 2.5 hours, both gels are removed from the freezer and the temperature is observed in the course of time, with the following results.

| T | 6% gel | 9% gel |
| --- | --- | --- |
| T = 0 | −5° C. | −5° C. |
| T = 1 h | −2.5° C. | −3.5° C. |
| T = 2 h | −2° C. | −3.5° C. |
| T = 3 h | −1° C. | −3.5° C. |
| T = 4 h | 0° C. | 0° C. |

Both gels are mechanically stable with hardly a tendency towards flowing.

What is claimed:

1. A method for cooling an organ, the method comprising directly contacting the organ with a cooling gel before or during transplantation of the organ, thereby cooling the organ, wherein the cooling gel is in a formable gel state and comprises 3% to 20% by weight of gelatin or a gelatin derivative.

2. The method of claim 1, wherein the gel is sterile.

3. The method of claim 1, wherein the gel is sterile and pyrogen-free.

4. The method of claim 1, wherein the gelatin is made from a natural collagen and the gelatin derivative is made by adding an agent to gelatin that changes the cross-linking properties of the gelatin.

5. The method of claim 1, wherein the gelatin derivative is succinyl gelatin, oxypolygelatin, or urea cross-linked gelatin.

6. The method of claim 1, wherein the gelatin or the gelatin derivative has a mean molecular weight of 25-45 kD.

7. The method of claim 1, wherein the gel comprises 5%-15% by weight of the gelatin or the gelatin derivative.

8. The method of claim 1, wherein the gel comprises 6%-20% by weight of the gelatin or the gelatin derivative, further comprises physiologically acceptable electrolytes, and has an osmolality of 280-650 mosmol/kg.

9. The method of claim 1, wherein the gel comprises 6%-10%, by weight, of the gelatin or the gelatin derivative.

10. The method of claim 1, wherein the gel comprises 6%-9% by weight of the gelatin or the gelatin derivative.

11. The method of claim 1, wherein the gel comprises 150-300 mmol/l sodium,
   5-10 mmol/l potassium,
   1.5-3 mmol/l magnesium,
   1.5-3 mmol/l calcium,
   100-200 mmol/l chloride, and
   30-60 mmol/l lactate.

12. The method of claim 1, wherein the gelatin derivative is succinyl gelatin.

13. The method of claim 1, wherein directly contacting the organ comprises enclosing the organ within the cooling gel.

* * * * *